US011104656B2

United States Patent
Roa Engel et al.

(10) Patent No.: US 11,104,656 B2
(45) Date of Patent: Aug. 31, 2021

(54) METHOD FOR PURIFYING AND REMOVING COLOR OF FDCA

(71) Applicant: Nederlandse Organisatie voor toegepast-natuurwetenschappelijk onderzoek TNO, s-Gravenhage (NL)

(72) Inventors: Carol Andrea Roa Engel, Delfgauw (NL); Johannes Van Der Meer, Loenen aan de Vecht (NL); Leonard Ferdinand Gerard Geers, Valkenburg (NL); Marc Crockatt, Hertogenbosch (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 0 days.

(21) Appl. No.: 16/958,255

(22) PCT Filed: Dec. 31, 2018

(86) PCT No.: PCT/NL2018/050894
§ 371 (c)(1),
(2) Date: Jun. 26, 2020

(87) PCT Pub. No.: WO2019/132663
PCT Pub. Date: Jul. 4, 2019

(65) Prior Publication Data
US 2021/0070722 A1    Mar. 11, 2021

(30) Foreign Application Priority Data
Dec. 29, 2017 (EP) .................................. 17211087
Mar. 16, 2018 (EP) .................................. 18162390

(51) Int. Cl.
*C07D 307/68* (2006.01)

(52) U.S. Cl.
CPC ........ *C07D 307/68* (2013.01); *C07B 2200/13* (2013.01)

(58) Field of Classification Search
CPC .......................... C07D 307/68; C07B 2200/13
USPC ........................................................ 549/485
See application file for complete search history.

(56) References Cited

U.S. PATENT DOCUMENTS

2012/0302768 A1* 11/2012 Janka ................... C07D 307/68
549/485

FOREIGN PATENT DOCUMENTS

JP          2017190316 A      10/2017

* cited by examiner

*Primary Examiner* — Taylor V Oh
(74) *Attorney, Agent, or Firm* — Banner & Witcoff, Ltd.

(57) ABSTRACT

The invention is based on the finding that when conducting crystallization of FDCA at high temperatures, the formation of significant amounts of colored byproduct can be reduced or even avoided when the FDCA mixture is kept at temperatures above 100° C. for less than 15 minutes. This is achieved by conducting the crystallization process in a continuous reactor. Accordingly, the method comprises the steps of feeding a mixture comprising undissolved FDCA and a solvent to a reactor; and dissolving FDCA by superheating the mixture in the reactor to a temperature of at least 130° C.; and crystallizing FDCA by cooling the mixture in the reactor, wherein the reactor is a continuous reactor and the residence time in the reactor zone wherein the FDCA mixture has a temperature above 100° C. is less than 15 minutes.

20 Claims, 4 Drawing Sheets

METHOD FOR PURIFYING AND REMOVING COLOR OF FDCA

RELATED APPLICATIONS

This application is a National Stage Application under 35 U.S.C. 371 of co-pending PCT application PCT/NL2018/050894 designating the United States and filed Dec. 31, 2018; which claims the benefit of EP application number 17211087.6 and filed Dec. 29, 2017 and EP application number 18162390.1 and filed Mar. 16, 2018 each of which are hereby incorporated by reference in their entireties.

The invention is directed to a method for purifying and/or removing, or at least reducing, the color of 2,5-furandicarboxylic acid (FDCA).

FDCA is an important compound for the production of biomass-derived polymers such as polyesters, polyamides, polyurethanes and the like. For instance, FDCA can be used as a building block in polyethylene-furanoate (PEF) which can be regarded as a bio-based alternative for the petrochemical-based polyethylene terephthalate (PET).

Biomass-derived FDCA is typically prepared in a one-step direct oxidation of HMF. HMF can be obtained from dehydrating carbohydrates (e.g. glucose and fructose) that are found in biomass. One-step direct oxidation of HMF to FDCA can for instance be carried out by thermochemical oxidation, biochemical oxidation or electrochemical oxidation.

The most common one-step direct oxidation of HMF to FDCA is thermochemical oxidation. In this process, HMF is converted to FDCA at elevated temperature (typically between 65 and 250° C., preferably 100-200° C.) in the presence of an oxidation catalyst. Such an oxidation reaction is well known in the art and for example described in WO 2011/043660 and WO 2015/030590.

The one-step direct electrochemical oxidation of FDCA from HMF by for instance using a Pt/C or a NiO(OH) anode is described in Vuyyuru et al., Catalysis Today 195 (2012), 144-154 and Grabowski et al., Electrochemica Acta 36 (1991), 1995, respectively. In Chadderdon et al., Green Chemistry 16 (2014), 3778-3786, the preparation of FDCA and other oxidation intermediates from HMF in an electrochemical cell using i.a. Pd—Au alloys is described.

WO2012064195 and Qin et al., Green Chemistry 17 (2015), 3718-3722 describe for instance one-step direct biochemical oxidation methods of HMF to FDCA by using genetically modified cells and an enzymatic toolbox respectively. As with other one-step oxidation methods, these one-step biochemical oxidation processes typically provide FDCA together with an undesirable high amount of side products.

A drawback of one-step direct oxidation methods is the rather unselective oxidation towards FDCA, partially due to the high instability of HMF, resulting in impure and colored (e.g. brown) FDCA. Certain byproducts formed in one-step direct oxidation reactions are undesirable as they may have a negative effect when applied in polymerization reactions of FDCA. In particular, certain byproducts formed can act as chain-terminators in polymerization reactions. For the production of polymers from FDCA, FDCA preferably has a purity of least 99.9 mol % and is preferably about colorless (white). FDCA of less than 99.9% purity generally results in undesirable premature chain termination during the polymerization process and a concomitant poor quality of the polymeric material. For example, brown FDCA generally results in colored polymeric materials, which are not suitable for most commercial uses, such as plastics drinks bottles and the like. As most commercial applications of FDCA require colorless material it will be evident that there is a need for methods to produce pure and colorless FDCA.

Due to the poor solubility of FDCA in standard solvents and its high boiling point, FDCA is notoriously difficult to purify by standard techniques such as recrystallization and distillation. Consequently, extensive downstream-processes are required for the purification of FDCA after its one-step production from HMF.

For example US 2013/0345452 is directed to a downstream-process, wherein FDCA is purified by conducting a hydrogenation reaction under mild conditions in the presence of a hydrogenation catalyst.

JP2017019031 6 discloses a purification method of FDCA comprising heating of the FDCA solution and subsequent precipitation of a solid.

It is accordingly desired to provide efficient techniques for purifying FDCA, such that less down-stream processing is required before a suitable purity and color reduction is obtained.

An object of the invention is to at least solve one of the problems mentioned above.

In particular, an object of the invention is to provide a method for purifying FDCA.

A further object of the invention to provide a method for purifying FDCA wherein no chemicals (e.g. reactants, catalysts or stabilizers) need to be added for the purification to work, except for a solvent.

A further object of the invention is to provide a method for removing, or at least reducing, the color of FDCA, in particular FDCA crystals.

At least one of these objects was met by providing a method comprising the steps of feeding a mixture of undissolved FDCA and a solvent to a reactor; and dissolving FDCA by superheating the mixture in the reactor; and crystallizing FDCA from the mixture by cooling the mixture; wherein the reactor is a continuous reactor comprising a reactor zone with a temperature above 100° C.; and wherein the residence time in said reactor zone is less than 15 minutes.

The inventors realized that it is desirable for FDCA crystallization to use superheating for dissolving FDCA. FDCA may show a significant increase in solubility above superheating conditions. For example, when using water as a solvent, the solubility of FDCA increases dramatically at temperatures beyond 130° C. However, the inventors also found that a significant amount of byproduct was formed at higher temperatures, in particular temperatures above 100° C. The byproduct is colored and its formation is therefore undesirable both in view of purity and color.

The inventors found that the formation of significant amounts of byproduct can be reduced or even avoided when the FDCA mixture is kept at temperatures above 100° C. only for a short time, i.e. less than 15 minutes. In principle, the shorter the time at the higher temperature, the less by-products are formed. However, a short high temperature time should not be detrimental to the desired dissolution of FDCA. Ideally, the time at higher temperature is just sufficient to dissolve all FDCA such that the impurities can be removed therefrom, followed by cooling to induce precipitation. Less than 15 minutes of heating at 100° C. or more was found to be sufficient, to also dissolve the largest pieces of FDCA. The inventors further found that this can best be achieved in a continuous reactor, which is therefore preferred. When scaling up the crystallization process in a standard crystallization set-up (typically conducted batchwise), the short time needed to avoid significant amounts of colored byproduct could not be achieved. Heating and cooling of large volumes of FDCA mixture is a slow process. Accordingly, the time necessary to dissolve all FDCA in the mixture and then to cool down the mixture proved to be too long to avoid the formation of significant amounts of colored byproduct. However, by using a continuous reactor, the FDCA mixture can be rapidly heated and cooled at different reactor zones, such that the duration for which the FDCA mixture is exposed to a temperature above 100° C. can be controlled. In this way, even large volumes of FDCA mixture can be heated, cooled and crystallized without having to expose (any part of) the FDCA mixture to a temperature above 100° C. for a duration of 15 minutes or more, 10 minutes or more or even 5 minutes or more. The resulting FDCA crystals showed a higher purity and reduced color compared to the crude FDCA in the initial FDCA mixture fed to the reactor.

The inventors further found that the presence of oxidizing agents such as oxygen in the water negatively affected the process. The removal of oxygen significantly improved the purification. Accordingly, superheating is preferably conducted under anaerobic conditions.

Anaerobic conditions can be achieved by using a degassed solvent in the method of the invention. Degasification is a technique to remove dissolved gases from a liquid. When degasifying the solvent, oxygen is removed from the solvent. The conditions in the solvent thus become anaerobic.

A degassed solvent can be obtained by degasifying the solvent. The skilled person will know suitable techniques to degasify the solvent. For example, degasification of the solvent may be conducted by pressure reduction, thermal regulation, membrane degasification, substituting oxygen with an inert gas (also known as sparging) or addition of a reductant. Degasification by pressure reduction or thermal regulation can be enhanced by sonication. Preferably, the solvent is degassed by sonication under reduced pressure.

The solvent is preferably degasified prior to mixing the solvent with FDCA.

The degassed solvent is kept under anaerobic conditions (e.g. under inert atmosphere or under elevated pressure) until used in the method of the invention. Thus, the dissolution of oxygen in the degassed solvent is prevented. The skilled person will know what conditions are suitable to achieve this.

The conditions in the reactor are preferably anaerobic as well. Such conditions prevent oxygen from dissolving in the solvent while flowing through the reactor. This may be achieved by flowing the mixture through the reactor under an inert atmosphere, e.g. under elevated pressure. Preferably, this is achieved by using a pressurized reactor, i.e. a reactor wherein the mixture is subjected to elevated pressure. For example, the pressure in the continuous reactor may be more than 1 bar to 50 bar, preferably 1.1-50 bar, even more preferably 1.5-40 bar, typically 2-30 bar.

The term "superheating" as used herein refers to heating a liquid to a temperature higher than its boiling point without boiling.

The term "boiling point" as used herein may refer to the standard boiling point of the liquid, which is the boiling point at a pressure of 1 bar. In case of the preferred solvent water, this temperature is 100° C.

The term "reactor zone having a temperature" as used herein refers to a zone in the reactor with a certain minimum temperature. The temperature throughout the zone does not have to be the same, but will always lie at or above the minimum temperature. Accordingly, any position in the reactor zone has a temperature at or above said certain minimum temperature. A reactor zone corresponds to a certain length of the reactor channel of the reactor, wherein the temperature is above said certain minimum temperature over its entire length. Thus, at any point in the reactor zone, the mixture will have a temperature at or above said minimum temperature. The reactor zone preferably corresponds to one continuous zone in the reactor (i.e. one continuous length of the reactor channel). Nevertheless, it may also be possible that said reactor zone consists of two or more reactor zones, each having a certain minimum temperature, with reactor zones of lower temperature in between the high temperature zones. However, such a configuration is generally not desirable, as heating and cooling should be kept to a minimum to keep the residence time as low as possible.

Figure 1:
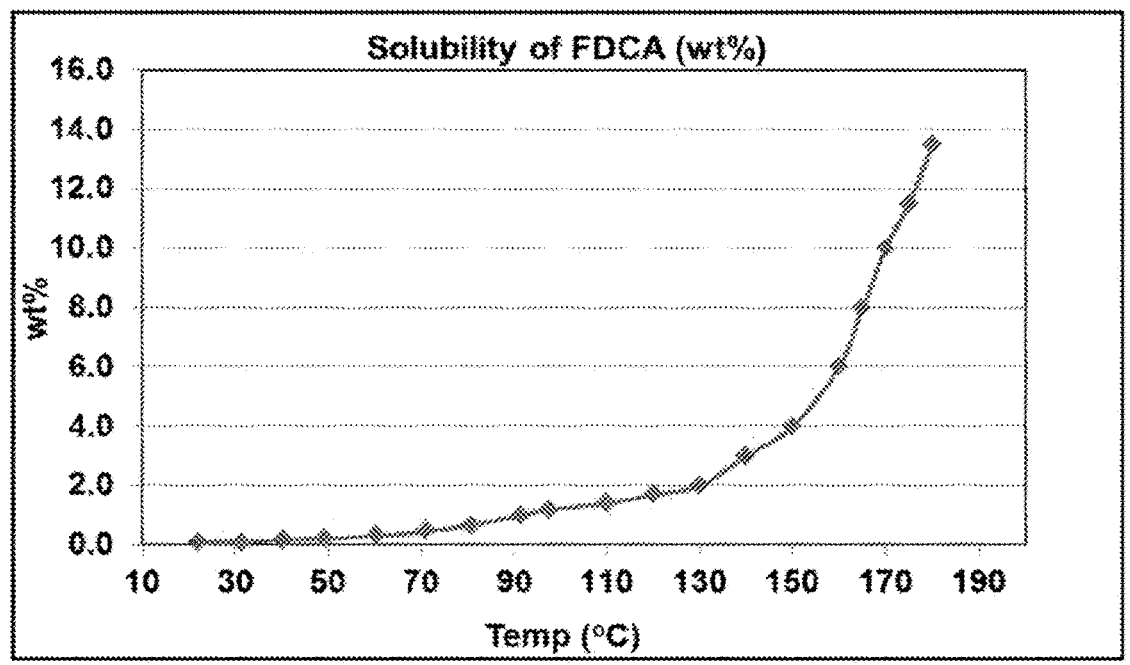
FIG. 1 shows the solubility of FDCA in water at different temperatures.

The method of the invention intends to reduce or avoid the formation of colored byproduct by exposing the FDCA mixture to high temperatures for only a short duration. Although the exact molecular structure of the byproduct formed is not known, the inventors expect that it will include humins and/or polymeric furanic compounds. The byproduct is formed at high temperatures, such as temperatures above 100° C. However, such temperatures cannot be avoided in view of the need for superheating the FDCA mixture and dissolving all FDCA present in the mixture. Accordingly, it is necessary to use a sufficiently high temperature to dissolve FDCA quickly, while at the same time subject the mixture to high temperatures for only a short duration to limit by-product formation.

The method of the invention provides a maximum duration that the FDCA mixture is exposed to high temperatures. Since the method is conducted in a continuous reactor, this maximum duration can suitably be expressed in terms of residence time. Accordingly, the method of the invention requires that the residence time in the reactor zone having a temperature above 100° C. (i.e. the reactor zone wherein the FDCA mixture has a temperature above 100° C.) is less than 15 minutes. The term "reactor zone having a temperature above 100° C." as used herein refers to those parts of the continuous reactor wherein the FDCA mixture has a temperature above 100° C. The residence time in this specific reactor zone may also be referred to herein as the "high temperature residence time".

The residence time in the reactor zone having a temperature above 100° C. is less than 15 minutes, preferably less than 10 minutes, more preferably less than 5 minutes, for example less than 3 minutes. In other words, the duration that any part of the FDCA mixture is exposed to temperatures above 100° C. is less than the afore-mentioned durations. Most preferably, the residence time is as short as possible. As soon as all FDCA has been dissolved, the temperature of the mixture should preferably be lowered again immediately. Nevertheless, a certain minimum residence time is generally required, as a certain amount of time is needed to heat the mixture, dissolve the undissolved FDCA and to cool the mixture. Accordingly, the residence time may be at least 1 minute, typically at least 2 minutes.

The size of the reactor zone having a temperature above the boiling point of the solvent can be easily controlled by the positioning and configuration of the heating and cooling elements in the continuous reactor. The residence time can be controlled by adjusting the flow rate of the FDCA mixture. By controlling the temperature of the reactor zone and the residence time, a good balance can be struck between quickly dissolving FDCA and minimizing the amount of byproduct formed during superheating.

The amount of byproduct formed will be larger when using a higher temperature in the reactor. Accordingly, when using a reactor with a reactor zone having temperatures higher than 120° C. or even 140° C., the residence time is preferably shorter than 15 minutes. This can be expressed by defining a reactor zone having a temperature above 120° C., above 140° C. or above 160° C. and its corresponding residence times. These reactor zones may be present in addition or instead of the reactor zone having a temperature above 100° C.

In case the continuous reactor comprises a reactor zone having a temperature above 120° C., the residence time in this particular zone is preferably less than 12 minutes, preferably less than 9 minutes, more preferably less than 6 minutes, even more preferably less than 3 minutes.

In case the continuous reactor comprises a reactor zone having a temperature above 140° C., the residence time in this particular zone is preferably less than 10 minutes, preferably less than 7 minutes, more preferably less than 4 minutes, even more preferably less than 3 minutes.

In case the continuous reactor comprises a reactor zone having a temperature above 160° C., the residence time in this particular zone is preferably less than 8 minutes, preferably less than 6 minutes, more preferably less than 3 minutes.

Similar to the reactor zone having a temperature above 100° C., the reactor zones described above also preferably are one continuous zone in the reactor.

The above-mentioned additional reactor zones are typically a part of the reactor zone having a temperature above 100° C., i.e. a subzone of the larger reactor zone having a temperature above 100° C. The residence time in the higher temperature zones should be particular short, while the residence time in the reactor zone having a temperature above 100° C. remains as defined further above.

The methods of the invention comprise three steps: (1) a feeding step, (2) a heating/dissolution step and (3) a crystallization step. These four steps are described in more detail below.

In the feeding step, a mixture comprising undissolved FDCA and a solvent is provided and is fed to a continuous reactor.

The mixture comprises FDCA and a solvent. The mixture is in particular a solid-liquid mixture. The mixture may be a slurry or a suspension. The FDCA may be partially dissolved in the solvent, but will comprise undissolved FDCA as well. Accordingly, the mixture will typically comprise a saturated solution of FDCA in the solvent.

The majority of the FDCA present in the mixture will generally be in undissolved (i.e. solid) form. The undissolved FDCA may be in crystalline or in amorphous form.

For example, the FDCA may be present as colored FDCA crystals (e.g. brown) or as a crude FDCA crystal product. These can for example be obtained in a one-step direct oxidation of HMF to FDCA. Accordingly, the method of the invention may comprise the step of preparing biomass-derived FDCA from HMF, in particular in a one-step direct oxidation of HMF. This step is conducted prior to the feeding step. The oxidation of HMF to FDCA may be carried out by thermochemical oxidation, biochemical oxidation or electrochemical oxidation, preferably by biochemical oxidation.

As the method of the invention relates to crystallization, the mixture preferably comprises a low amount of impurities. Accordingly, the concentration of compounds other than the solvent and FDCA is preferably below 3 wt. %, more preferably below 1 wt. %, even more preferably below 0.5 wt. %, even more preferably below 0.1 wt. %, based on the total weight of the mixture. As it is not intended to conduct any type of reaction in the continuous reactor, preferably no reactants or catalysts are present in the mixture. In one embodiment, the method is conducted in the absence of a catalyst, reactants or both. In particular, the method is conducted in the absence of a hydrogenation catalyst.

The solvent in the mixture may be any solvent that can be suitably used in FDCA crystallization processes. The solvent may be water or an organic solvent. Examples of suitable organic solvents are alcohols, ethers, esters, ketones, carboxylic acids, amides, nitriles, sulfoxides, sulfones, aromatic compounds, and halogenated solvents.

Suitable examples of alcoholic solvents are C1-C4 alcohols (e.g. methanol and ethanol) and C2-C4 diols (e.g. ethylene glycol). Suitable examples of amide solvents are dimethyl formamide (DMF), N-methyl-2-pyrrolidone (NMP), dialkyl acetamides (e.g. dimethyl acetamide (DMA)), N-alkyl acetamides (e.g. ethyl acetamide) and ethyl formamide. Suitable examples of sulfoxide solvents are C1-C4 dialkyl sulfoxide, e.g. dimethyl sulfoxide (DMSO)). A suitable examples of a sulfone is sulfolane. Further examples of suitable solvents are ethers, such as C1-C8 ethers (e.g. diethyl ether and tert-butyl methyl ether). The term "Cx-Cy" as used herein refers to a compound containing a number of carbon atoms of at least x, but not more than y.

Furthermore, suitable examples of ketones are C1-C8 ketones (e.g. acetone, butanone, and methyl isobutyl ketone). Suitable examples of carboxylic acids are C1-C6 carboxylic acids (e.g. acetic acid). Suitable examples of nitriles are C1-C6 nitriles (e.g. acetonitrile). Suitable examples of halogenated solvents are chlorinated solvents, in particular C1-C8 chlorinated solvents, such as chlorinated hydrocarbons (e.g. dichloromethane). Suitable examples of esters are alkyl carbonates (e.g. C1-C6 alkyl carbonates, such as ethyl acetate) and dialkyl carbonates (e.g. dimethyl carbonate). Suitable examples of aromatic compounds are C5-C10 aromatic compounds such as toluene. Further, a cyclic heterocycle, such as a C5 or C6 heterocycle comprising oxygen as the heteroatom (e.g. 2-methyltetrahydrofuran) can be used as the solvent. Preferably, the solvent is selected from the group consisting of water, methanol, ethanol, ethylene glycol, DMF, NMP, DMA, ethyl acetamide, ethyl formamide, DSMO and sulfolane. Most preferably, the solvent is water. When using water as a solvent, the solubility of FDCA increases dramatically at temperatures beyond 130° C. This makes the temperature range at which the method of the invention is conducted particularly advantageous. Accordingly, the mixture is preferably an aqueous mixture comprising undissolved FDCA. When using a solvent other than water, it may be preferable to dissolve FDCA in the solvent by superheating the mixture to a temperature above the boiling point of the solvent, preferably at least 10° C. above, for example at least 20° C. or at least 30° C. above said boiling point.

The mixture may have a concentration of at least 1.5 wt. % FDCA, preferably at least 2 wt. % FDCA, even more preferably at least 3 wt. % FDCA, even more preferably at least 5 wt. % FDCA, even more preferably at least 8 wt. % FDCA, even more preferably at least 12 wt. % FDCA, based on the total weight of the mixture. Due to the high temperature used in the dissolution step, such high FDCA concentrations can be suitably used in the method of the invention.

The mixture described above is fed in step (1) of the method of the invention to a continuous reactor. Since the mixture comprises solids, the continuous reactor should preferably be capable of processing slurries and/or suspensions. This will reduce the risk of clogging the reactor.

The mixture is preferably mixed while residing in the reactor. In this way, clogging of the reactor can be reduced or even avoided. Also, this has the advantage that the possible formation of hot spots can be prevented in the reactor. The reactor may for example comprise one or more stationary baffles for obstructing the flow of the mixture through the reactor. The baffle may be for example be provided as an insert in the reactor tube. The reactor may also comprise an oscillating baffle or other types of moving elements capable of providing mixing in the reactor. Preferably, the reactor comprises one or more curved channels. In a preferred embodiment, the reactor comprises multiple curved channels in combination with a stationary baffle or with a moving element capable of providing mixing in the reactor. An example of a suitable continuous reactor is for example a helix reactor. The multiple curved channels in a helix reactor provide for the presence of Dean vortices which can effectively mix the mixture. Another example of a suitable continuous reactor is an oscillating baffled reactor (OBR).

The continuous reactor generally has a reactor channel, through which the mixture flows. The reactor channel may comprise one or more straight or shaped (sub)channels, such as the one or more curved channels mentioned above. The reactor channel may comprise two openings, viz. an inlet for the mixture to enter the reactor and an outlet for the mixture to exit the reactor. The reactor channel may have a diameter of at least 0.5 mm, preferably at least 1 mm. A typical range for the diameter is 0.5-250 mm, preferably 0.5-100 mm, more preferably 1-50 mm, for example 2-20 mm. Preferably, the reactor channel has a tubular shape, in which case the reactor channel may be referred to as a reactor tube. The diameter of the reactor channel is preferably at least 10 times as large as the diameter of the largest particle present in the mixture. By using a reactor channel with the diameter indicated above, the volume of mixture passing through the channel can be quickly heated and cooled. In this way, the residence time of the high-temperature zones can be controlled.

In one embodiment, the continuous reactor is operated using an oscillating flow. In other words, the mixture flows through the reactor channel with an oscillating flow. This means that the mixture is flowed alternately in backward and forward direction in the channel of the continuous reactor. This may provide for increased control of the residence time and the possibility of using a relatively small reactor. A process using such oscillating or reversed flow is described e.g. in WO 2014/058320. The flow may for example be reversed 10 or more times, 50 or more times or even 100 or more times during passage of the mixture through the channel of the continuous reactor. The flow can be suitably reversed by applying high pressure at one end of the channel and/or low pressure at another end of the channel, and/or by providing alternating high and low pressure at one or more positions in the channel. Alternatively, the flow can be reversed by axially moving actuators in the channel.

Preferably, the reactor is an anaerobic reactor.

The method of the invention further comprises the step of dissolving FDCA by superheating the mixture in the reactor. This step may be referred to as the heating/dissolution step.

In the heating/dissolution step of the method of the invention, the FDCA is dissolved by superheating the mixture in a continuous reactor. The term "superheating" as used herein refers to heating a liquid to a temperature higher than its boiling point without boiling. The skilled person will know how this can be achieved, for example by using an elevated pressure in the reactor. FDCA may show a significant increase in solubility above superheating conditions.

In the heating/dissolution step, the undissolved FDCA is dissolved in the solvent. In order to obtain pure crystals in the crystallization step, it is necessary that as much FDCA as possible, most preferably all FDCA, is dissolved in the solvent in this step. Accordingly, the mixture obtained in the heating/dissolution step preferably comprises less than 0.5 wt. % undissolved FDCA, more preferably less than 0.1 wt. % FDCA, most preferably no undissolved FDCA at all. Thus, the mixture obtained in the heating/dissolution step may be an FDCA solution.

The continuous reactor comprises a reactor with a temperature of at least 100° C. Accordingly, the FDCA mixture is heated to at least this temperature. However, in order to rapidly dissolve FDCA, it is generally desirable to heat the FDCA to a higher temperature. Preferably, FDCA is dissolved by superheating the mixture at a temperature of at least 130° C. In certain embodiments, for example when processing mixtures with particular high FDCA concentrations, it may be preferred to heat to even higher temperatures, e.g. to a temperature of at least 150° C. or of at least 170° C. It is generally not desirable to conduct in the dissolution step at too high temperatures. FDCA will generally be superheated at a temperature not higher than 240° C., for example not higher than 210° C. or 190° C. Very high temperatures may not be desirable in view of dealing with high pressures and possible decomposition of the compounds in the mixture.

In order to avoid boiling of the solvent, an elevated pressure in the continuous reactor may be used. Such a reactor may be referred to as a pressurized reactor. The pressure in the continuous reactor is generally in the range of 1 to 50 bar, depending on the temperature zone of the reactor. The higher temperature zones in the reactor will typically have a higher pressure. At temperatures higher than 100° C., the pressure may be in the range of 1.5-40 bar, preferably 2-30 bar. In case an oscillatory flow is used, the pressure is preferably 10-30 bar. When the continuous reactor is operated with a continuous flow (i.e. using same flow velocity throughout the reactor channel), the pressure is preferably 3-20 bar in the high temperature zones of the reactor.

The method of the invention further comprises a crystallization step. In the crystallization step, the mixture is cooled. By cooling the mixture, the FDCA that is dissolved in the solvent will recrystallize in the mixture. At least part of the cooling may be conducted in the reactor. Typically, the mixture is at least cooled in the reactor to a temperature below the boiling point of the solvent. The pressure typically used in the reactor for superheating is no longer necessary at this point. When the mixture is no longer superheated, it can be further cooled outside the reactor. Alternatively, the entire crystallization step may also be conducted in the reactor. The crystallization step may be conducted under anaerobic conditions. This can be achieved by conducting the crystallization step in a pressurized continuous reactor.

In the crystallization step, the mixture is cooled, preferably to a temperature below 100° C., more preferably below 50° C. Typically, the mixture is simply cooled to room temperature. As the solubility of FDCA is low, it will generally already start to crystallize at high temperatures, e.g. at temperatures above 100° C. While cooling the mixture, FDCA crystals are obtained. These crystals have a higher purity and will typically have a lighter color compared to the crystals that were fed to the reactor.

Preferably, the total residence time of the FDCA mixture in the continuous reactor is short. The total residence time may be less than 15 minutes, preferably less than 12 minutes, more preferably less than 9, even more preferably less than 5 minutes, for example less than 3 minutes.

Alternatively, the residence time of the FDCA in the continuous reactor may also be significantly longer than 15 minutes. As the speed of cooling may have an effect on particle size distribution, it is preferred to cool the mixture slowly, especially in the range of 0-100° C., for example back to room temperature or even lower. In case the entire crystallization step is conducted in the reactor, this may mean that the residence time in the reactor may be more than 30 minutes or even more than 1 hour.

The flow rate of the mixture through the reactor lies in the range of 2-120 reactor volumes per hour, preferably in the range of 4-60 reactor volumes per hour. The reactor volume used is not particularly critical, as the process is intended to be scalable. In practice, the reactor volume may for example lie in the range of 0.05 to 100 L, typically in the range of 0.1 to 20 L.

As already discussed above, the FDCA mixture should be exposed to the high temperature only for a short time, which should be long enough to dissolve the FDCA, but short enough to avoid signification formation of colored byproduct. Accordingly, the high temperature residence time should be less than 15 minutes, as defined above. The high temperature residence time is determined by the dimensions of the reactor zone wherein the FDCA mixture has a temperature above 100° C., as well as the flow rate of the FDCA mixture through the reactor and the temperature in the reactor. By varying these two parameters, the skilled person will know how to configure the reactor to achieve the desired result.

In a further aspect, the invention is directed to a method for reducing the color of FDCA crystals. The method comprises the same steps as described above for the method of the invention of the first aspect. The mixture may be prepared by mixing colored FDCA crystals with a solvent, preferably water.

The method is illustrated by the experimental examples below.

Comparative Example 1: Batch Process

Crude FDCA (27 g, 97.7% pure—obtained from a one-step direct oxidation of HMF) and demineralized water (300 ml) were charged in an autoclave vessel, which was mounted with a magnetic overhead stirrer. The content of the vessel was heated from 20 to 180° C. within 20 minutes and subsequently cooled down to 20° C. within 20 minutes. Upon filtration and washing with demineralized water (2×300 mL, 8° C.) pure FDCA (24 g, >99.5% pure) was obtained.

Example 2: Continuous Flow Process

A 10 wt. % slurry of crude FDCA in demineralized water was prepared. This slurry was then fed into a tubular continuous flow reactor having a temperature of 150-190° C., and fed at a rate such that the residence time in the reactor was less than 15 minutes. During this period, a suitable technique was applied to prevent settling of the solids (pulsations). After the desired residence time, the contents of the reactor were cooled to room temperature to facilitate precipitation, and the formed FDCA was isolated by filtration and washed with demineralized water.

Figure 2:
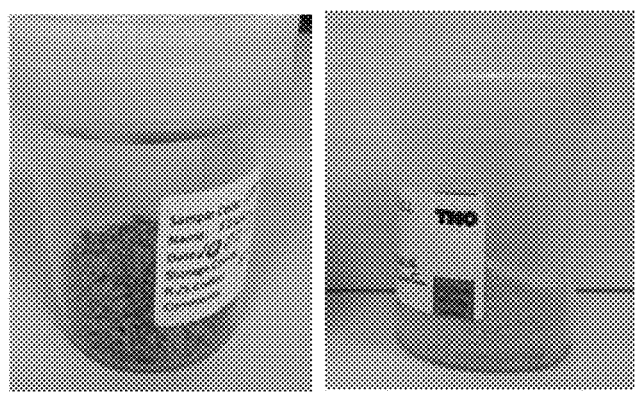
FIG. 2 shows photographs of crude FDCA obtained in a one-step direct oxidation reaction from HMF (left) and of the same FDCA after purification with the method of the invention (right).

Photographs were taken of the crude FDCA and the FDCA obtained after purification. These are shown in FIG. 2. The photographs show that the colour of the purified FDCA was of much lighter colour than the colour of the crude FDCA. After equilibration, the purity was found to be >99.5%.

Example 3: Organic Solvent Process

This example shows that the method can be conducted using a wide variety of organic solvents.

Crude FDCA (180 mg—obtained from a one-step direct oxidation of HMF) and a degassed (by sonication under reduced pressure) organic solvent (300 ml) were charged to a pressure reactor, which was equipped with a magnetic stirrer.

The content of the vessel was heated from 130° C. and held for 10 minutes, and subsequently quickly cooled down to 20° C. The resulting suspension was filtrated and washed with with demineralized water (2×1 mL, 8° C.)

The experiment was repeated using the following solvents: acetic acid, acetone, acetonitrile, dichloromethane, dimethyl carbonate, 1,4-dioxane, ethanol, ethyl acetate, methyl ethylketone, methanol, methyl isobutylketone, tert-butyl methylether, 2-methyltetrahydrofuran, and toluene.

Upon filtration and washing, a lighter FDCA than the starting material was obtained for all solvents, with the exception of methanol which yielded a darker product. Especially in the cases of 1,4-dioxane and ethanol, much lighter solids (comparable, or lighter than those achieved in water) were obtained. In the case of ethanol, analysis showed that a small amount of the ethyl ester had been produced (~2.5 mol %).

Figure 3:
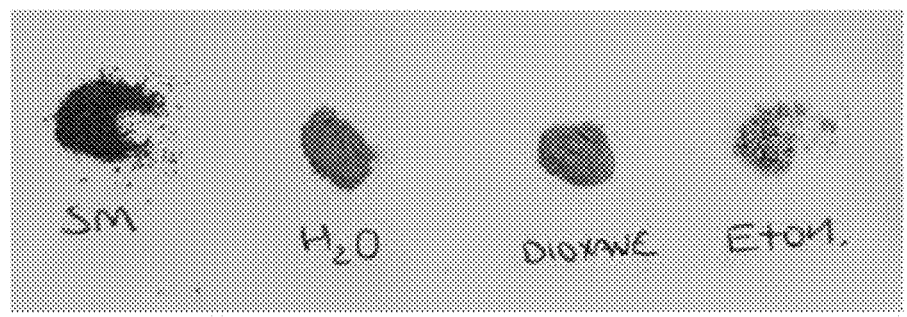
FIG. 3 shows photographs of crude FDCA obtained in a one-step direct oxidation reaction from HMF (left, "SM") and of the same FDCA after purification with the method of the invention using $H_2O$, dioxane and ethanol respectively.

FIG. 3 shows photographs of the unpurified HMF used (left, "SM") and of the HMF purified with the method of the invention using water as the solvent (middle left, "$H_2O$"), dioxane as the solvent (middle right, "dioxane") and ethanol as the solvent (right, "EtOH"). Even though the conditions in this experiment were not optimized for water or any of the other organic solvents, it is still evident that a significant colour reduction can be achieved by the method of invention for all these three solvents.

Example 4: Influence of Heating Time on Decomposition

Figure 4:
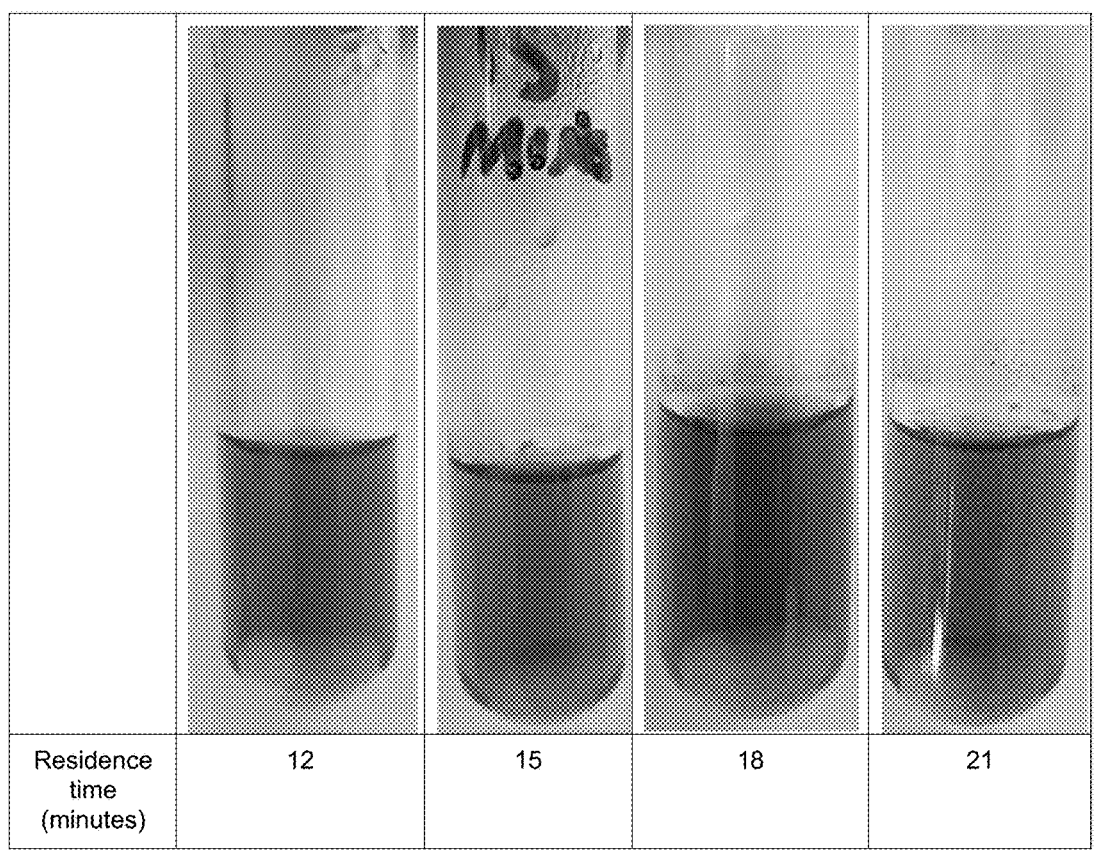
FIG. 4 shows photographs of the influence of heating time on decomposition of the FDCA mixture after heating.

In a reaction vessel, 60 mg of FDCA was dissolved over time in 3 ml of deionised water at a temperature of 130° C. On heating, around 5 minutes was needed to allow the solid to dissolve. Following this, samples were taken at 12, 15, 18 and 21 minutes. The samples were photographed at these intervals (FIG. 4). As shown in the photos, it was observed that after 12 minutes a light solution is observed, but after 15 minutes some black solid by-products started to form on the inside of the tube around the top of the liquid. After 18 minutes the solution was clearly darker brown in color with more black material having formed on the inside of the tube around the top of the liquid.

Example 5: Influence of Heating Time on Decomposition

In another experiment, the influence of heating time on the color of the precipitate after cooling was investigated. A total of nine samples were prepared by mixing 200 mg of FDCA in 2 mL $H_2O$. These samples were heated for the temperature and time as indicated in Table 1.

TABLE 1

| Sample | Temp. (° C.) | Time (min) |
|---|---|---|
| 1 | 140 | 5 |
| 2 | 160 | 5 |
| 3 | 180 | 5 |
| 4 | 140 | 10 |
| 5 | 160 | 10 |
| 6 | 180 | 10 |
| 7 | 140 | 15 |
| 8 | 160 | 15 |
| 9 | 180 | 15 |

Figure 5:
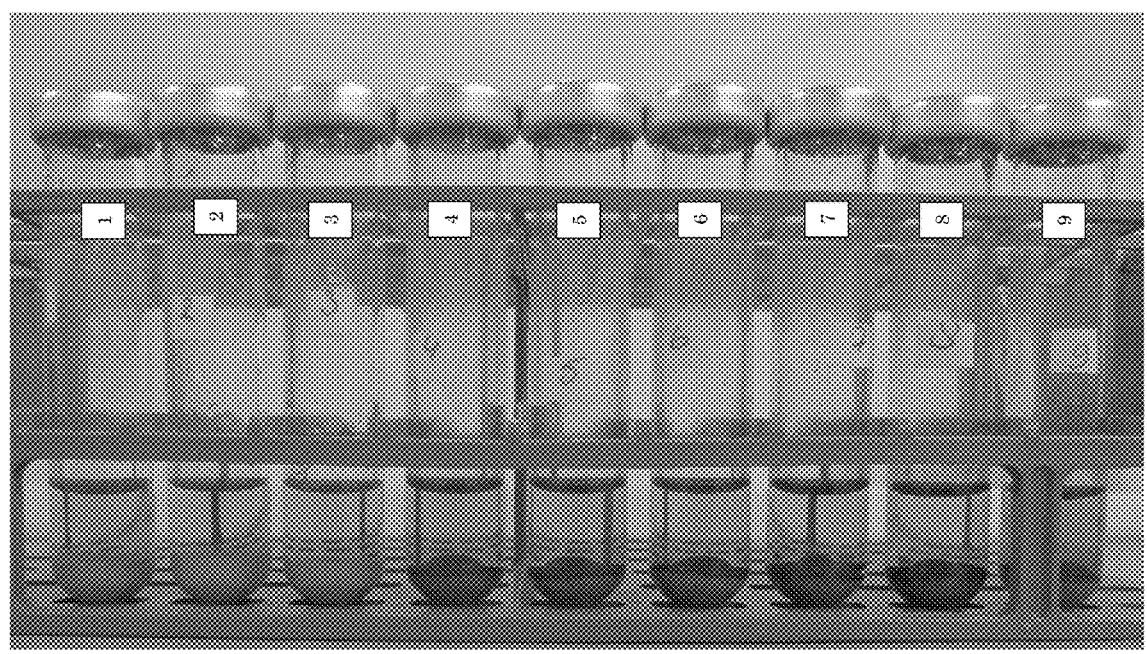
FIG. 5 shows photographs of the influence of heating time on decomposition of the FDCA mixture after heating and followed by cooling.

After heating as indicated in Table 1, the samples were cooled and photographed (FIG. 5, samples 1-9 are labeled accordingly). It was found that prolonged heating resulted in formation of black solid by-products.

The invention claimed is:

1. A method for purifying 2,5-furandicarboxylic acid ("FDCA") comprising the steps of
feeding a mixture comprising undissolved FDCA and a solvent to a reactor; and
dissolving FDCA by superheating the mixture in the reactor; and
crystallizing FDCA from the mixture by cooling;
wherein the reactor is a continuous reactor comprising a reactor zone having a temperature above 100° C.; and
wherein the residence time in the reactor zone having a temperature above 100° C. is less than 15 minutes.

2. A method for reducing the color of FDCA crystals comprising the steps of
optionally degassing a solvent; and
preparing a mixture by mixing colored FDCA crystals with the solvent; and
feeding the mixture comprising FDCA crystals to a reactor; and
dissolving FDCA by superheating the mixture in the reactor; and
crystallizing FDCA from the mixture by cooling,
wherein the reactor is a continuous reactor comprising a reactor zone having a temperature above 100° C.; and
wherein the residence time in the reactor zone having a temperature above 100° C. is less than 15 minutes.

3. The method according to claim 1 or 2, wherein superheating is conducted under anaerobic conditions.

4. The method according to claim 1, wherein the reactor has a reactor channel having a diameter in the range of 0.5-250 mm.

5. The method according to claim 1, wherein the solvent is selected from the group consisting of water, alcohols, aromatic compounds, chlorinated solvents, ethers, esters, ketones, carbonates, amides, nitriles, sulfoxides and sulfones.

6. The method according to claim 1, wherein the solvent is degassed water and FDCA is superheated to a temperature of at least 130° C. in the dissolution step.

7. The method according to claim 1, wherein the residence time of the reactor zone having a temperature above 100° C. is less than 5 minutes.

8. The method according to claim 1, wherein the residence time of FDCA in the continuous reactor is less than 15 minutes.

9. The method according to claim 1, wherein the continuous reactor has a helix shape.

10. The method according to claim 1, wherein the mixture is mixed in the reactor using a static mixer or by oscillating baffles.

11. The method according to claim 1, wherein the mixture that is fed to the continuous reactor has an FDCA concentration of at least 2 wt. %, based on the total weight of the mixture.

12. The method according to claim 1, wherein the mixture that is fed to the continuous reactor has an FDCA concentration of at least 5 wt. %, based on the total weight of the mixture.

13. The method according to claim 1, wherein superheating is conducted at an elevated pressure of 1.5-40 bar.

14. The method according to claim 1, wherein the method is conducted in the absence of a catalyst or reactants.

15. The method according to claim 1, wherein the reactor comprises a reactor zone having a temperature of at least 130° C., wherein the residence time in said reactor zone having a temperature of at least 120° C. is less than 12 minutes.

16. The method of claim 2 wherein superheating is conducted under anaerobic conditions.

17. The method of claim 2 wherein the residence time of FDCA in the continuous reactor is less than 15 minutes.

18. The method of claim 2 wherein the mixture that is fed to the continuous reactor has an FDCA concentration of at least 5 wt. %, based on the total weight of the mixture.

19. The method of claim 2 wherein superheating is conducted at an elevated pressure of 1.5-40 bar.

20. The method of claim 2 wherein the method is conducted in the absence of a catalyst or reactants.

* * * * *